United States Patent [19]

Hammond et al.

[11] 4,138,401

[45] Feb. 6, 1979

[54] [3,2-g] PYRANOQUINOLINE DERIVATIVES

[75] Inventors: Peter R. Hammond, Livermore; Erhard J. Schimitschek, San Diego; John A. Trias, La Mesa, all of Calif.

[73] Assignee: The United States of America as represented by the Secretary of the Navy, Washington, D.C.

[21] Appl. No.: 671,236

[22] Filed: Mar. 29, 1976

[51] Int. Cl.$^2$ .......................................... C07D 491/04
[52] U.S. Cl. ...................................... 546/89; 250/199
[58] Field of Search ........ 260/287 T, 287 CF, 287 D, 260/287 C

[56] References Cited

U.S. PATENT DOCUMENTS 3,629,290  12/1971  Cairns et al. ...................... 260/287 R
3,923,836  12/1975  Bender et al. ...................... 260/345.2

OTHER PUBLICATIONS

Hammond, "Blue-green Lasing Dyes," (1973), pp. 6 and 16–19.
Adams (ed. in chief) Organic Reactions, vol. VII, pp. 7–11.

Primary Examiner—Donald G. Daus
Assistant Examiner—David E. Wheeler
Attorney, Agent, or Firm—R. S. Sciascia; Roy Miller; Don R. Mollick

[57] ABSTRACT

2-Keto-6,7,8,9-tetrahydro-2H-pyrano(3,2-g)-quinoline and 2-keto-9-methyl-6,7,8,9-tetrahydro-2H-pyrano(3,2-g)-quinoline, compounds useful as laser dyes, are prepared from 7-hydroxy-1,2,3,4-tetrahydroquinoline.

2 Claims, No Drawings

[3,2-g] PYRANOQUINOLINE DERIVATIVES

BACKGROUND OF THE INVENTION

1. Field of the Invention

This invention relates to laser dyes, particularly to heterocyclic dyes containing hetero nitrogen and oxygen atoms, and more particularly to coumarin derivatives.

2. Description of the Prior Art

In the search for laser dyes operating at the blue-green transmission window of sea water, many substituted coumarins have been examined. Many such compounds have been reported to lase, as reported, for example by G. A. Reynolds and K. H. Drexhage in *Optics Communications*, Vol. 13, No. 3, p. 222, March 1975; P. R. Hammond and R. L. Atkins in *J. Hetero. Chem.*, Vol. 12, p. 1061, October 1975; and P. R. Hammond in U.S. patent application Ser. No. 526,760, filed Nov. 25, 1974.

Two problems associated with liquid laser dye solutions, well known to those skilled in the art, are photochemical stability under flash and continuous wave excitation and efficiency of laser output power compared to electrical input into the flash lamp.

SUMMARY OF THE INVENTION

The compounds disclosed herein are 2-keto-6,7,8,9-tetrahydro-2H-pyrano(3,2-g)-quinoline and its 9-methyl derivative, 2-keto-9-methyl-6,7,8,9-tetrahydro-2H-pyrano(3,2-g)-quinoline. They are prepared from 7-hydroxy-1,2,3,4-tetrahydroquinoline. They are efficient laser dyes, and, in the case of the 9-methyl derivative, very stable.

DESCRIPTION OF THE PREFERRED EMBODIMENT

The compounds of the present invention and their method of synthesis may be represented by the following formula:

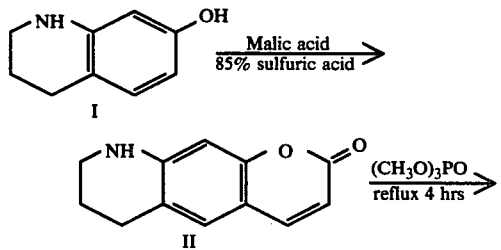

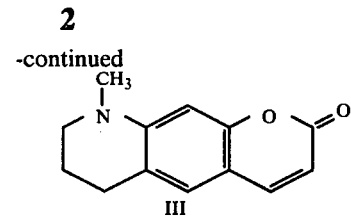

7-Hydroxy-1,2,3,4-tetrahydroquinoline (hereinafter termed "compound I") may be prepared by a modified Skraup synthesis used in the preparation of quinolines.

Compound I 12.0 g, malic acid 50 g and 85% sulfuric acid made from ice 4.0 g and 100 ml of the concentrated acid (96%) were mixed and heated at 110° for an hour and fifteen minutes. The cooled mixture was diluted with ice and water, brought to pH8 with about 200 g sodium carbonate and extracted overnight with dichloromethane.

Dry column chromatography isolates the condensation product. The dried solution was evaporated to a small volume for implanting on alumina and was chromatographed using ethyl acetate as the developing solvent. The fluorescent band was cut out and eluted with methanol and evaporated to give 1.12 g of orange crystals. Crystallization from acetonitrile/water using decolorizing charcoal gave yellow plates of 2-keto-6,7,8,9-tetrahydro-2H-pyrano(3,2-g)-quinoline (Compound II), mp 244.0°–244.5°. C, 71.6; H, 5.49; N, 7.10 was found. $C_{12}H_{11}NO_2$ requires C, 71.7; H, 5.48; N, 6.97%.

2-Keto-6,7,8,9-tetrahydro-2H-pyrano(3,2-g)-quinoline (compound II), 600 mg, was refluxed in trimethyl phosphate for four hours. The mixture was boiled with 150 ml water, filtered, and cooled producing 390 mg of the 9-methyl derivative (compound III). Crystallization from methanol/water gave yellow-green plates mp 165.5°–166°. C, 72.7; H, 6.15; N, 6.44 was found; $C_{13}H_{13}NO_2$ requires C, 72.6; H, 6.05; N, 6.52%. Nuclear magnetic resonance and infrared spectra were in accord with the proposed structures.

The compounds disclosed herein feature an amino group as part of a fused heterocyclic ring structure which resists rotation into stereoisomers. This improves fluroescent quantum yields.

The compounds herein disclosed also incorporate the basic coumarin ring structure which is responsible for the laser action association with the known charge transfer process between the two rings.

In the case of compound III, the 9-methyl group improves stability by eliminating the N-H bond which becomes strongly acidic when the nitrogen atom is involved in the lasing electron transition. The lack of large hydrophobic substituents improves the solubility of both compounds in water.

What is claimed is:

1. 2-keto-6,7,8,9-tetrahydro-2H-pyrano(3,2-g)-quinoline.
2. 2-keto-9-methyl-6,7,8,9-tetrahydro-2H-pyranol 3,2-g)- quinoline.